United States Patent
Choi et al.

(10) Patent No.: US 11,382,525 B2
(45) Date of Patent: Jul. 12, 2022

(54) HANDHELD BLOOD-FLOW IMAGING DEVICE

(71) Applicant: The Regents of the University of California, Oakland, CA (US)

(72) Inventors: Bernard Choi, Elk Grove, IL (US); Sean White, Tustin, CA (US)

(73) Assignee: The Regents of the University of California, Oakland, CA (US)

( * ) Notice: Subject to any disclaimer, the term of this patent is extended or adjusted under 35 U.S.C. 154(b) by 610 days.

(21) Appl. No.: 15/946,523

(22) Filed: Apr. 5, 2018

(65) Prior Publication Data

US 2018/0289269 A1  Oct. 11, 2018

Related U.S. Application Data

(60) Provisional application No. 62/483,212, filed on Apr. 7, 2017.

(51) Int. Cl.
*A61B 5/026* (2006.01)
*A61B 5/00* (2006.01)
*A61B 5/021* (2006.01)

(52) U.S. Cl.
CPC .......... *A61B 5/0261* (2013.01); *A61B 5/0082* (2013.01); *A61B 5/0033* (2013.01); *A61B 5/0075* (2013.01); *A61B 5/021* (2013.01); *A61B 5/441* (2013.01); *A61B 5/489* (2013.01)

(58) Field of Classification Search
CPC .... G01N 21/17; A61B 5/0077; A61B 5/0079; A61B 5/44
See application file for complete search history.

(56) References Cited

U.S. PATENT DOCUMENTS

| | | | | |
|---|---|---|---|---|
| 4,805,971 A | * | 2/1989 | Fantone | G02B 13/14 359/354 |
| 6,032,071 A | * | 2/2000 | Binder | A61B 5/0059 356/369 |
| 6,491,715 B1 | * | 12/2002 | Abels | A61B 18/203 128/898 |
| 2004/0176701 A1 | * | 9/2004 | Fujii | A61B 5/411 600/556 |
| 2008/0123106 A1 | * | 5/2008 | Zeng | A61B 5/445 356/600 |
| 2013/0053701 A1 | * | 2/2013 | Wiest | A61B 5/445 600/476 |
| 2015/0025343 A1 | * | 1/2015 | Gareau | A61B 5/444 600/328 |

OTHER PUBLICATIONS

Boas et al. "Laser speckle contrast imaging in biomedical optics", Journal of Biomedical Optics 15(1), 011109 (Jan./Feb. 2010) (Year: 2010).*

(Continued)

*Primary Examiner* — Colin T. Sakamoto
(74) *Attorney, Agent, or Firm* — Gavrilovich, Dodd & Lindsey LLP

(57) ABSTRACT

The present invention relates to devices and methods of use thereof for real time blood flow measurements of skin. In one embodiment, the device is a compact laser speckle imaging, or LSI, system that is integrated with a dermatoscope. In another embodiment, the device allows the user to diagnose a disease or condition in an individual, or as part of an overall treatment regimen.

8 Claims, 18 Drawing Sheets

(56) References Cited

OTHER PUBLICATIONS

Briers et al., "Laser speckle contrast imaging: theoretical and practical limitations" Journal of Biomedical Optics, vol. 18(6), Jun. 27, 2013, p. 066018-1-066018-9 (Year: 2013).*

Stucker et al., "Increased laser Doppler flow in skin tumors corresponds to elevated vessel density and reactive hyperemia", Skin Research and Technology, 12: 1-6, 2006, Abstract (Year: 2006).*

Ragol et al., "Static laser speckle contrast analysis for noninvasive burn diagnosis using a camera-phone imager" Journal of Biomedical Optics 20(8), 086009 (Aug. 2015) (Year: 2015).*

* cited by examiner

Raw speckle image

Speckle flow index map

Median(Δ) = 921 P.U.
(n = 15)

Movement Noise = (Instrument Noise + Movement Noise) - (Instrument noise)

Movement Noise = 0.00734 – 0.00364

Movement Noise = 0.0037

Figure 23.

| Finger | Forearm |
|---|---|
| Signal COV = 0.0517 | Signal COV = 0.060 |
| Noise COV = 0.00734 | Noise COV = 0.00734 |
| Signal:Noise = 7.04 | Signal:Noise = 8.17 |

Figure 24.

| Finger | Forearm |
|---|---|
| Signal COV = 0.0517 | Signal COV = 0.060 |
| Noise + Repeatability COV = 0.0125 | Noise + Repeatability COV = 0.0125 |
| Signal:Noise = 4.13 | Signal:Noise = 4.8 |

Figure 25.

| Finger | Forearm |
|---|---|
| Signal Amplitude = 0.0134 | Signal Amplitude = 0.0456 |
| Noise Amplitude = 0.0018 | Noise Amplitude = 0.0018 |
| Signal:Noise = 7.44 | Signal:Noise = 25.3 |

Figure 26.

| Finger | Forearm |
|---|---|
| Signal Amplitude = 0.0134 | Signal Amplitude = 0.0456 |
| Noise + Repeatability Amplitude = 0.00267 | Noise + Repeatability Amplitude = 0.00267 |
| Signal:Noise = 5.02 | Signal:Noise = 17.1 |

Signal Amplitude = 0.023

Noise Amplitude = 0.0018

Signal:Noise = 12.7

HANDHELD BLOOD-FLOW IMAGING DEVICE

CROSS-REFERENCE TO RELATED APPLICATIONS

The present application claims the benefit of priority under 35 U.S.C. § 119(e) of provisional application Ser. No. 62/483,212, filed Apr. 7, 2017, the contents of which are hereby incorporated by reference.

STATEMENT REGARDING FEDERALLY SPONSORED RESEARCH

The invention was made with government support under Grant No. EB015890 awarded by the National Institutes of Health (NIH). The government has certain rights in the invention.

FIELD OF THE INVENTION

The present disclosure relates to the medical field, and more specifically, handheld devices for simultaneous visual inspection and blood flow measurements and mapping of tissue.

BACKGROUND OF THE INVENTION

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Dermatoscopes are commonly utilized for the qualitative visual inspection of skin lesions. While automated image processing techniques and varied illumination strategies have been used to aid in structural analysis of lesions, robust quantification of functional information, such as blood flow, is largely unknown. Current solutions to provide maps of blood flow involve large, expensive devices that are impractical for routine use in clinics.

Thus, besides the dermatoscope, there is a need in the art for the development of novel, quantitative, and effective devices to aid in disease diagnosis, prognosis, and treatment.

SUMMARY OF THE INVENTION

Various embodiments include a device, comprising a dermatoscope comprising an illuminating light source and a magnifying optic, wherein the dermatoscope is integrated with a laser speckle imaging (LSI) system. In another embodiment, the illuminating light source is a broadband light source. In another embodiment, the device is handheld. In another embodiment, the device is adapted so that the areas being visually inspected and measured using the LSI are co-localized. In another embodiment, the device allows real time blood flow measurements. In another embodiment, the device provides blood flow measurements of skin during visual inspection of a subject. In another embodiment, the device provides functional information of tissue simultaneously with visual inspection of the subject. In another embodiment, areas are being visually inspected and measured using LSI are co-localized. In another embodiment, the device includes a CMOS camera. In another embodiment, the device is described in FIGS. 3-6 herein. In another embodiment, the device is described in FIG. 15 herein.

Other embodiments include a method of evaluating a subject, comprising providing a device comprising a laser speckle imaging (LSI) system integrated with a dermatoscope, and evaluating the subject. In another embodiment, the device may be used for cancer screening. In another embodiment, the method comprises simultaneous visual inspection and blood flow measurement. In another embodiment, the method comprises simultaneous visual inspection and mapping of tissue. In another embodiment the region of tissue being inspected by dermatoscopy is the same region being measured using LSI. In another embodiment, the device may be used for visually observing and quantifying blood flow changes in skin nevi. In another embodiment the device may be used for visually observing and quantifying blood flow changes associated with skin inflammation, irritation, wounds, burns, allergies, scars, infections, dermatitis, acne, keratosis, psoriasis, and/or Rosacea. In another embodiment, the method comprises simultaneous visual inspection and mapping of tissue blood flow and hemodynamics.

Various embodiments include a method of measuring blood flow in a subject, comprising obtaining laser speckle imaging (LSI) measurements, and validating flow measurements. In another embodiment, validating flow measurements comprises acquiring LSI data from a tissue-simulating phantom with syringe pump-controlled flow of optically scattering fluid across a physiologically relevant range. In another embodiment, the method provides an overall map of overall blood flow. In another embodiment, the method provides robust quantification of functional information of the subject. In another embodiment, the subject is a human.

Other embodiments include a method of diagnosing a condition or disease in a subject, comprising providing a device comprising a compact laser speckle imaging (LSI) system integrated with a dermatoscope, making an evaluation of the subject using the device, and diagnosing the condition or disease based on the evaluation. In another embodiment, the disease is cancer. In another embodiment, the disease is skin cancer. In another embodiment, the method comprises simultaneous visual inspection and blood flow measurement.

Other features and advantages of the invention will become apparent from the following detailed description, taken in conjunction with the accompanying drawings, which illustrate, by way of example, various embodiments of the invention.

DESCRIPTION OF THE DRAWINGS

Exemplary embodiments are illustrated in referenced figures. It is intended that the embodiments and figures disclosed herein are to be considered illustrative rather than restrictive.

FIG. 23 depicts, in accordance with embodiments herein, signal to noise measurements, COV version.

FIG. 24 depicts, in accordance with embodiments herein, signal to noise measurements, COV version.

FIG. 25 depicts, in accordance with embodiments herein, signal to noise measurements, amplitude version.

FIG. 26 depicts, in accordance with embodiments herein, signal to noise measurements, amplitude version.

DETAILED DESCRIPTION

Figure 1:
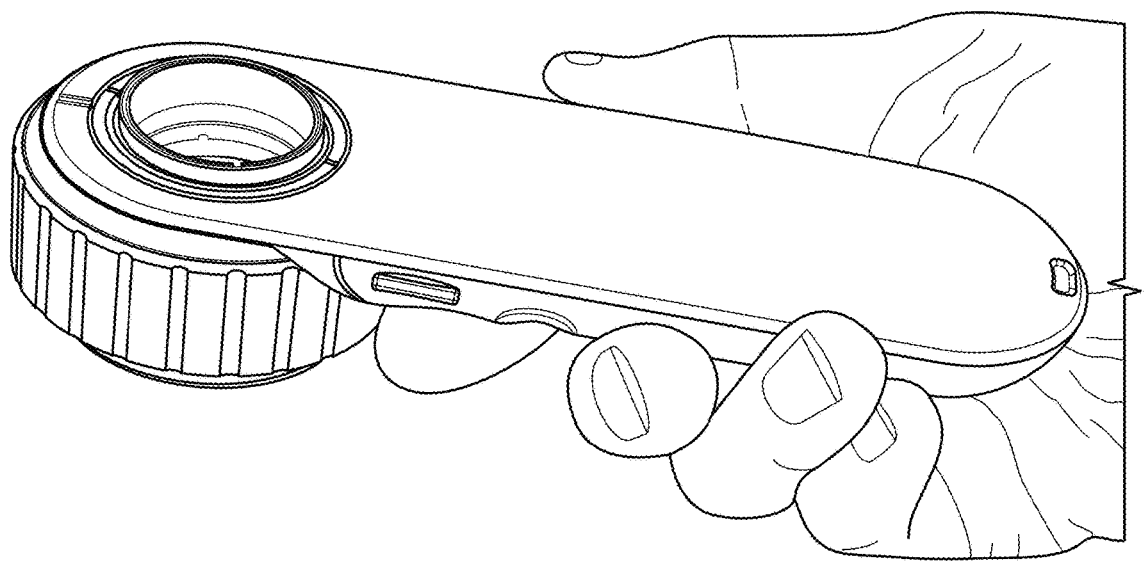
FIG. 1 depicts, in accordance with embodiments herein, an example of a dermatoscope. As further described herein, there are shortcomings of the dermatoscope as it is commonly used amongst dermatologists. For example, it may be used for structural information only. It does not allow measurement of tissue function. However, it is used to assess 5.4 M cases of non-melanoma skin cancer annually in the US, despite its ability to distinguish only structural information. Structural features of skin lesions are alone often inadequate for accurate diagnoses, which in turn leads potentially unnecessary biopsy. The ability to measure blood flow may help improve diagnosis by providing functional information in addition to structural information. Tumors, for example, exhibit atypically high blood flow, with perfusion in skin tumors being greater than normal skin. Perfusion differentiates varying skin tumor types, for example, and blood flow measurement can improve diagnostic accuracy.
Figure 2:
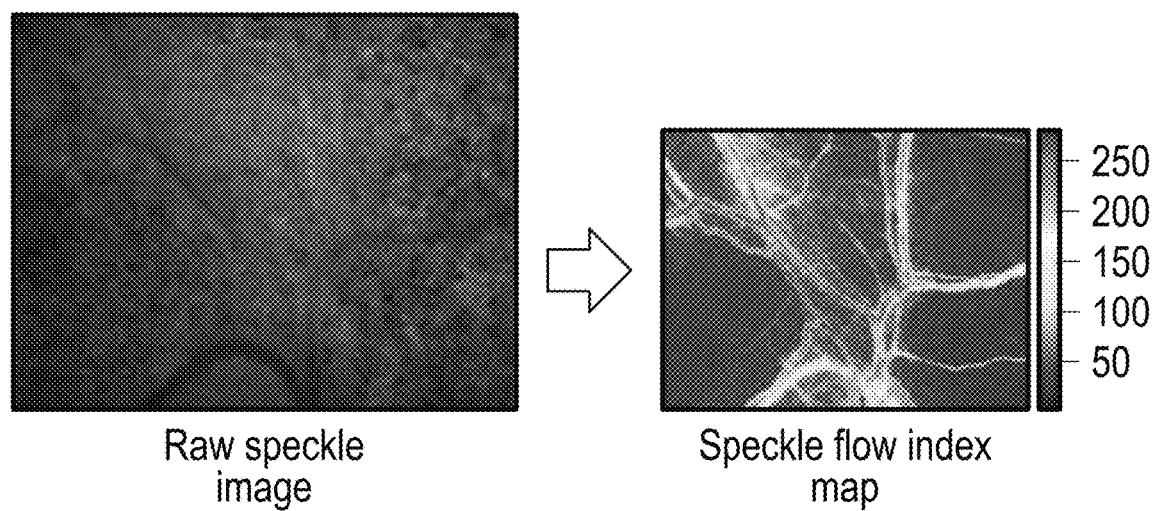
FIG. 2 depicts, in accordance with embodiments herein, blood flow measurements with Laser Speckle Imaging (LSI).
Figure 3:
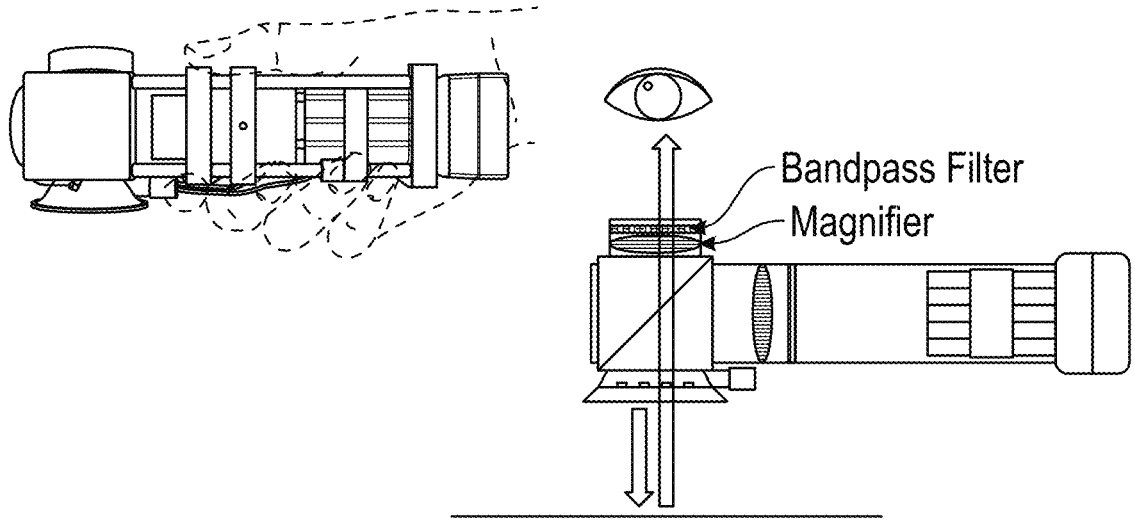
FIG. 3 depicts, in accordance with embodiments herein, a Laser Speckle Imaging Dermatoscope example and diagram. In accordance with various embodiments herein, the diagram includes a demonstration of possible locations for a bandpass filter, as well as a magnifier.
Figure 4:
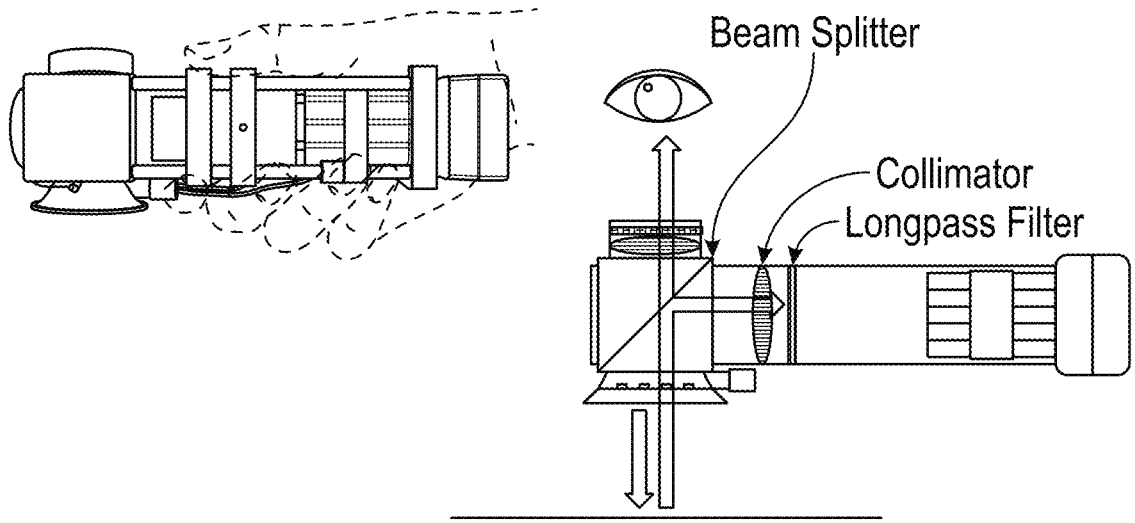
FIG. 4 depicts, in accordance with embodiments herein, a Laser Speckle Imaging Dermatoscope example and diagram. In accordance with various embodiments herein, the diagram includes a demonstration of possible locations for a beam splitter, a collimator, and a longpass filter.
Figure 5:
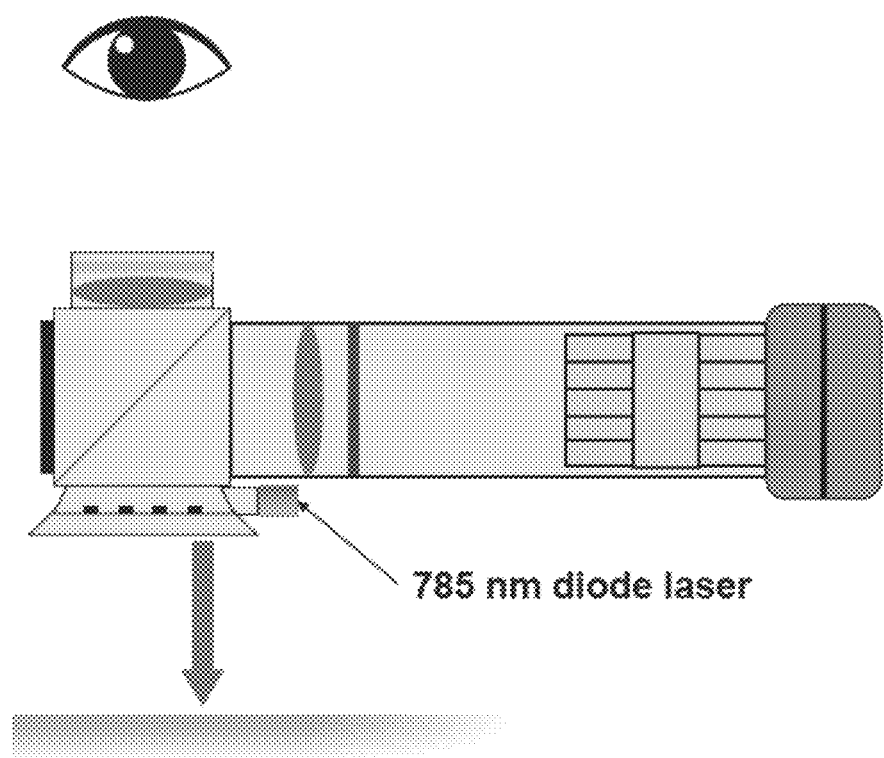
FIG. 5 depicts, in accordance with embodiments herein, a Laser Speckle Imaging Dermatoscope example and diagram. In accordance with various embodiments herein, the diagram includes a demonstration of a possible location for a diode laser, or specifically, for a 785 nm diode laser.
Figure 6:
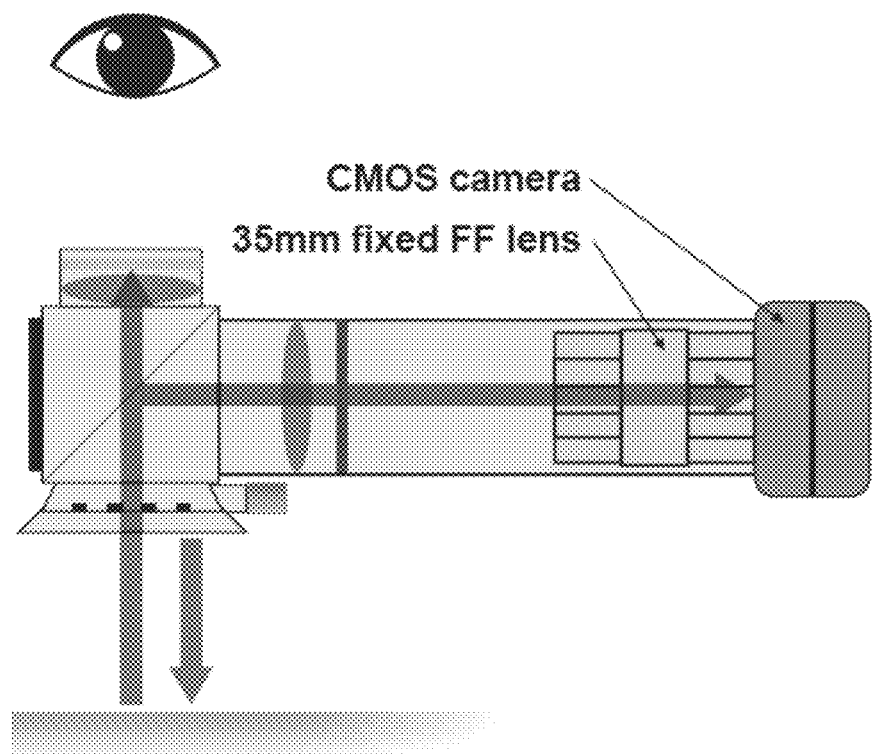
FIG. 6 depicts, in accordance with embodiments herein, a Laser Speckle Imaging Dermatoscope example and diagram. In accordance with various embodiments herein, the diagram includes a demonstration of possible locations for a camera, such as a CMOS camera. Or, for example, a 35 mm fixed FF lens.
Figure 7:
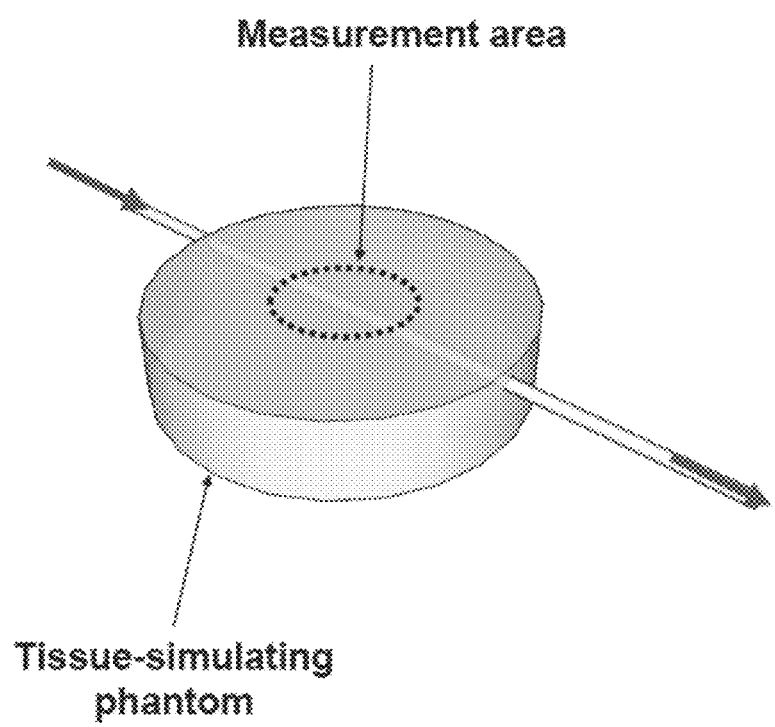
FIG. 7 depicts, in accordance with embodiments herein, a diagram for in vitro validation for sensitivity analysis.
Figure 8:
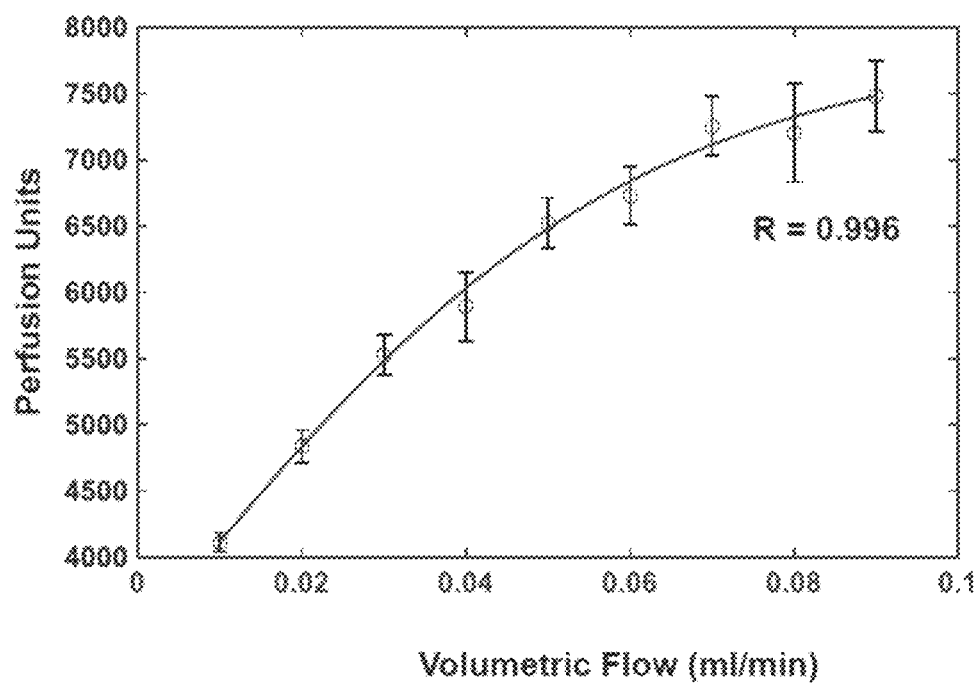
FIG. 8 depicts, in accordance with embodiments herein, a chart of results for in vitro validation for sensitivity analysis.
Figure 9:
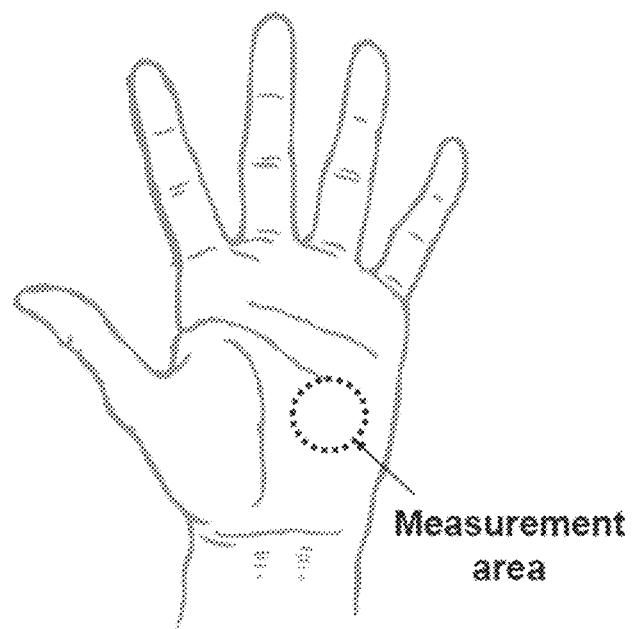
FIG. 9 depicts, in accordance with embodiments herein, a diagram of the measurement area in the palm of a hand for in vivo validation, in this case for example skin measurement.
Figure 10:
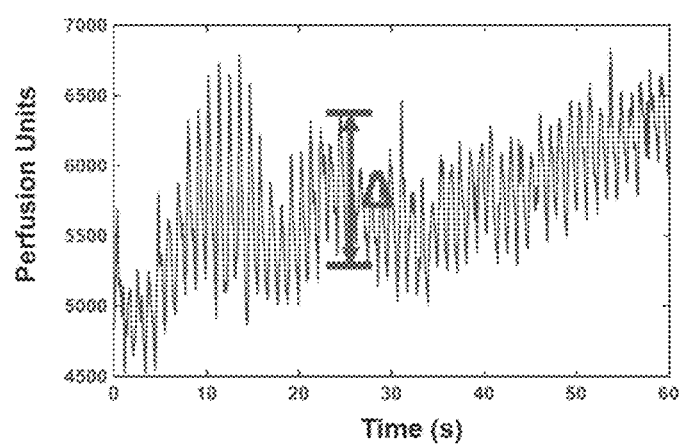
FIG. 10 depicts, in accordance with embodiments herein, a chart describing in vivo validation, in this case for signal to noise analysis. In this instance, the signal to noise ratio is 12:1.
Figure 11:
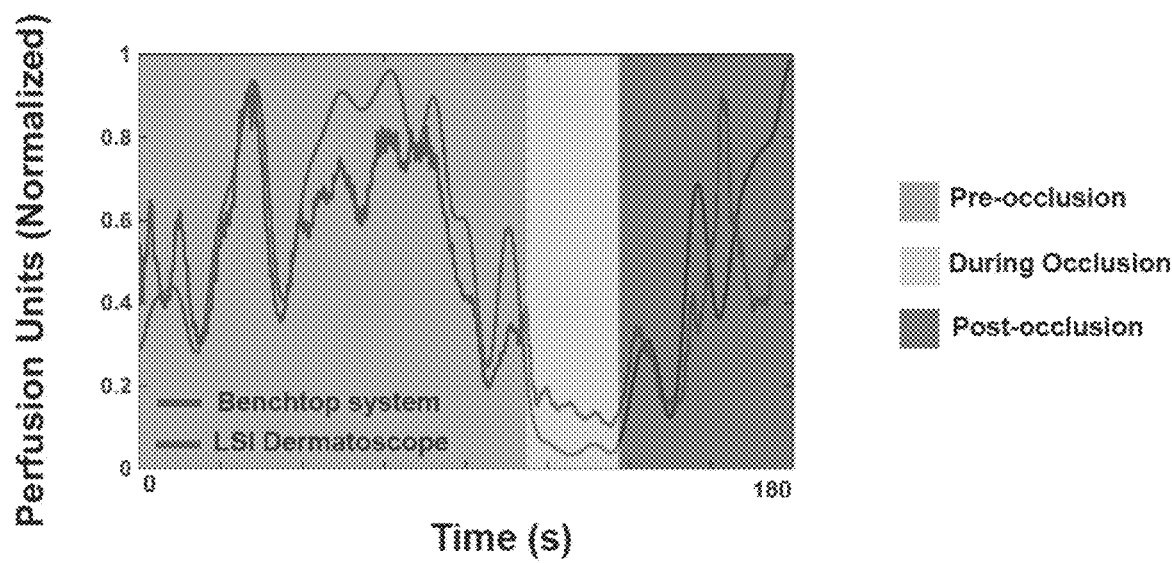
FIG. 11 depicts, in accordance with embodiments herein, a chart describing in vivo validation, including PORH Response vs. Reference. The chart depicts the first column as pre-occlusion, the second as during occlusion, and the third as post-occlusion.
Figure 12:
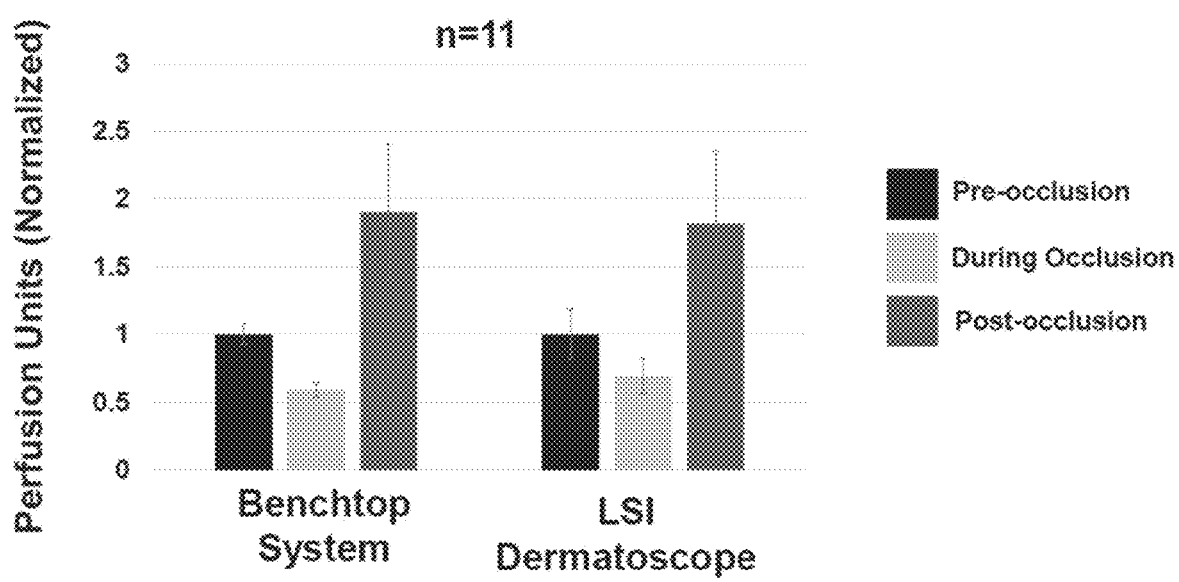
FIG. 12 depicts, in accordance with embodiments herein, bar graph charts describing in vivo validation, including PORH Response vs. Reference, for both Benchtop system, and for LSI Dermatoscope.
Figure 13:
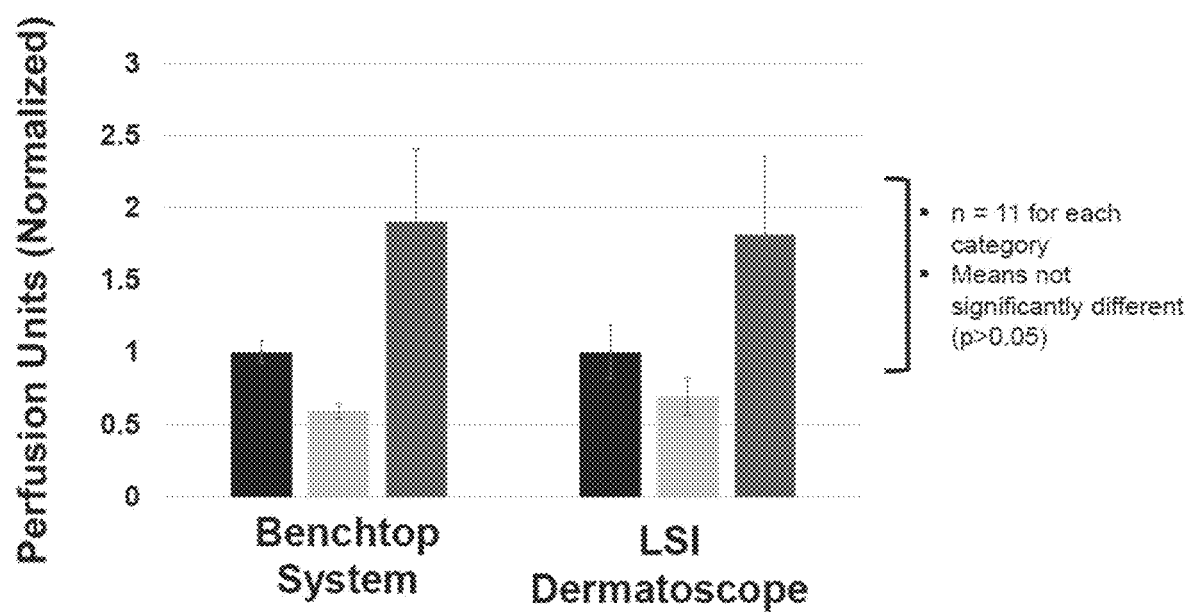
FIG. 13 depicts, in accordance with embodiments herein, bar graph charts describing in vivo validation, including PORH Response vs. Reference, for both Benchtop system, and for LSI Dermatoscope.
Figure 14:
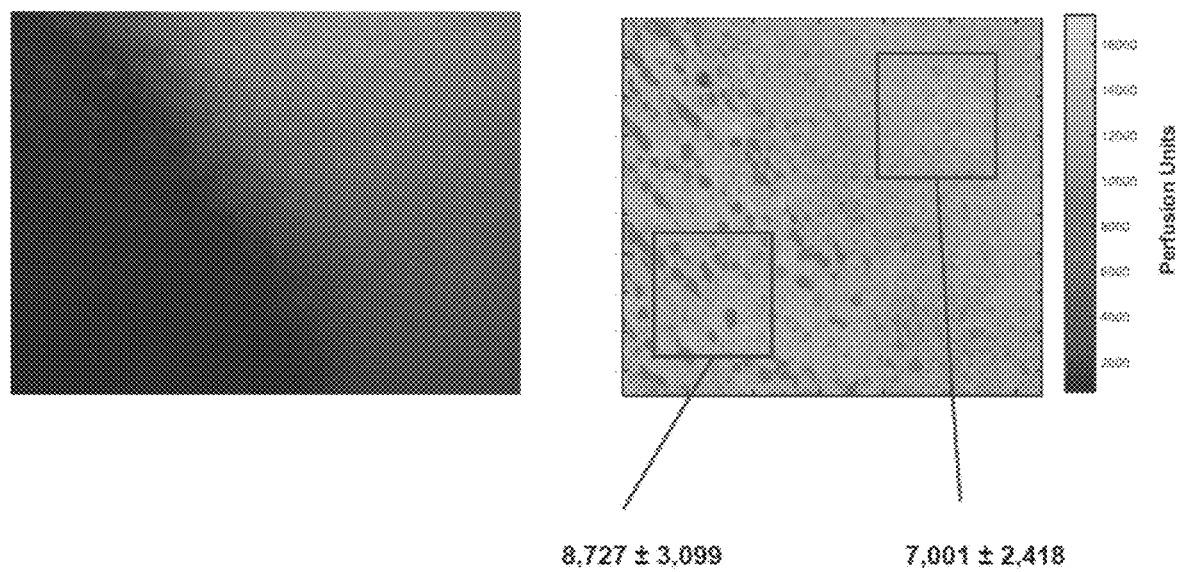
FIG. 14 depicts, in accordance with embodiments herein, an example of in vivo validation with Nevi Measurement.
Figure 15:
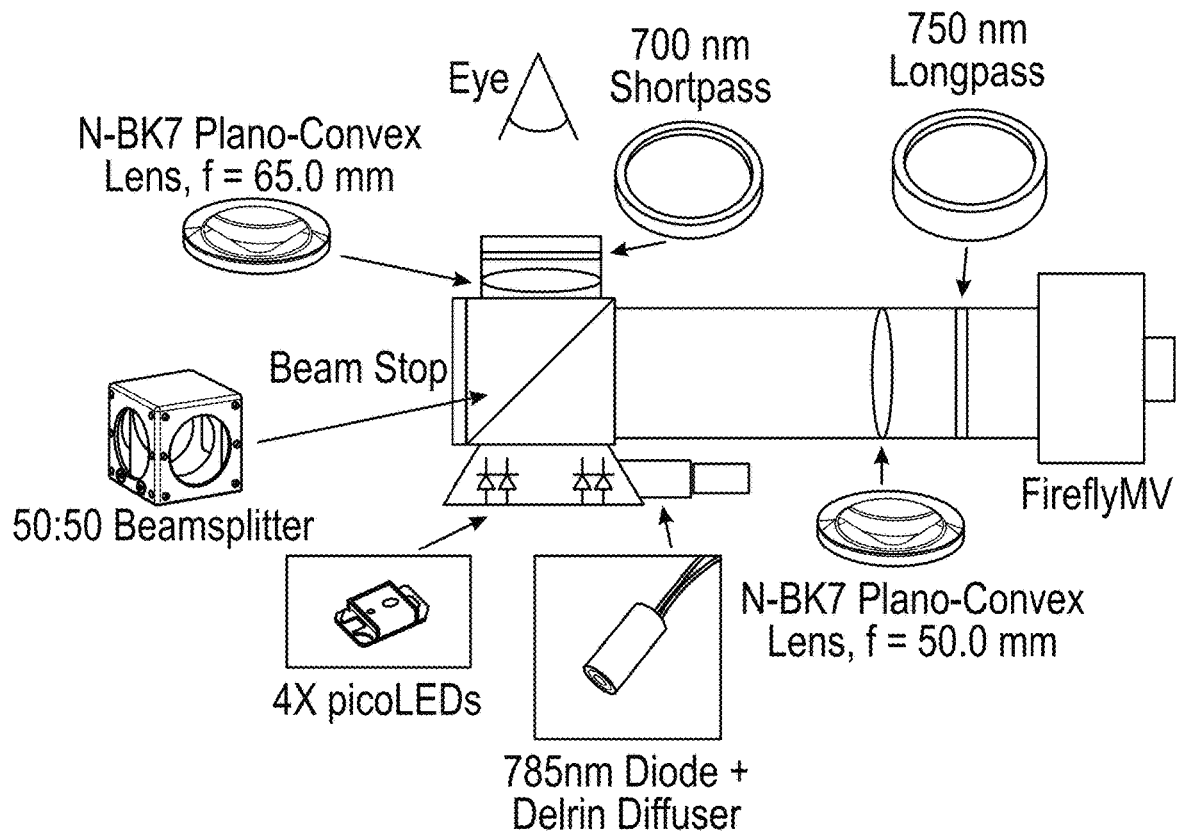
FIG. 15 depicts, in accordance with embodiments herein, an example of a LSI dermatoscope.
Figure 16:
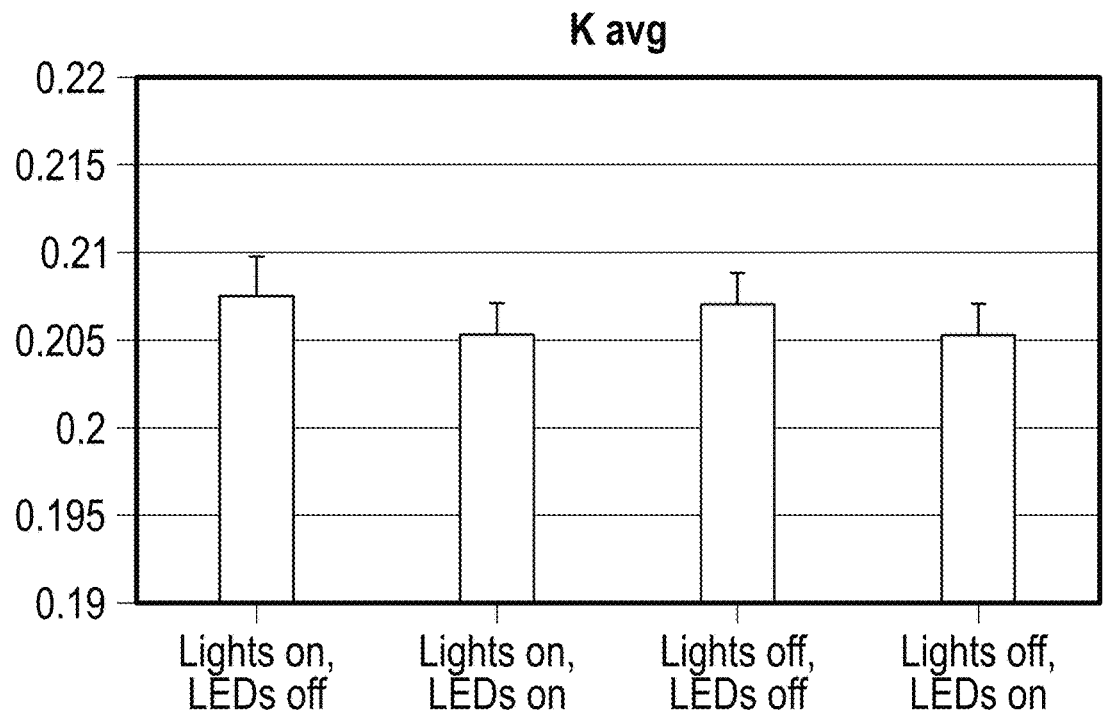
FIG. 16 depicts, in accordance with embodiments herein, a chart describing light rejection analysis.
Figure 17:
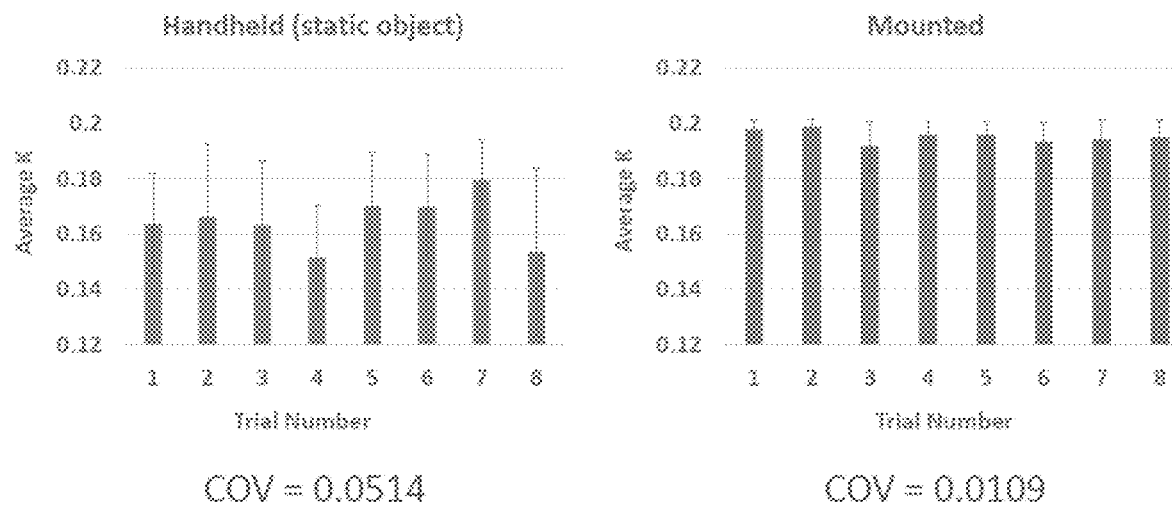
FIG. 17 depicts, in accordance with embodiments herein, charts describing repeatability measures.
Figure 18:
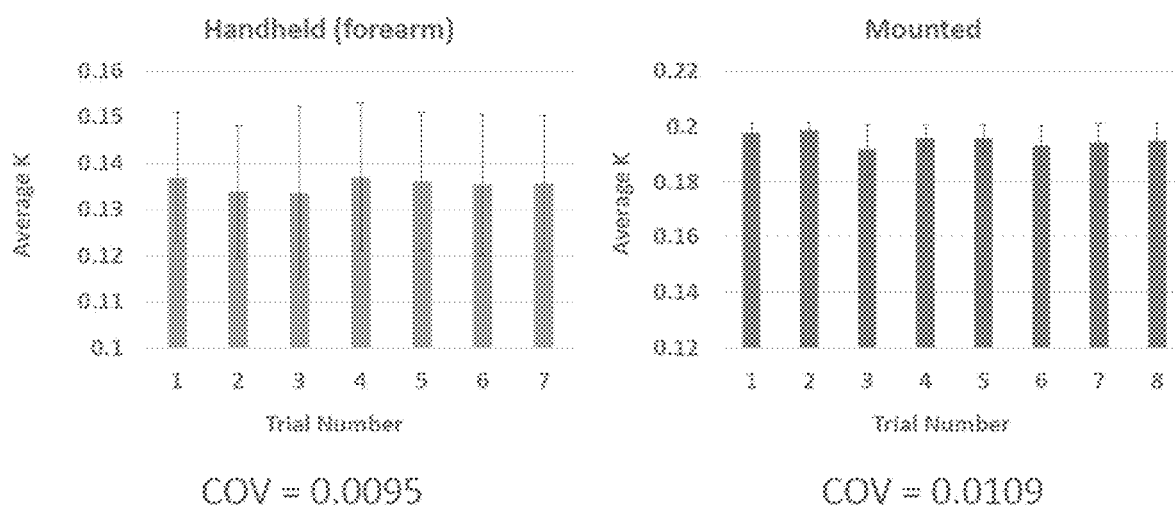
FIG. 18 depicts, in accordance with embodiments herein, charts describing repeatability measures.
Figure 19:
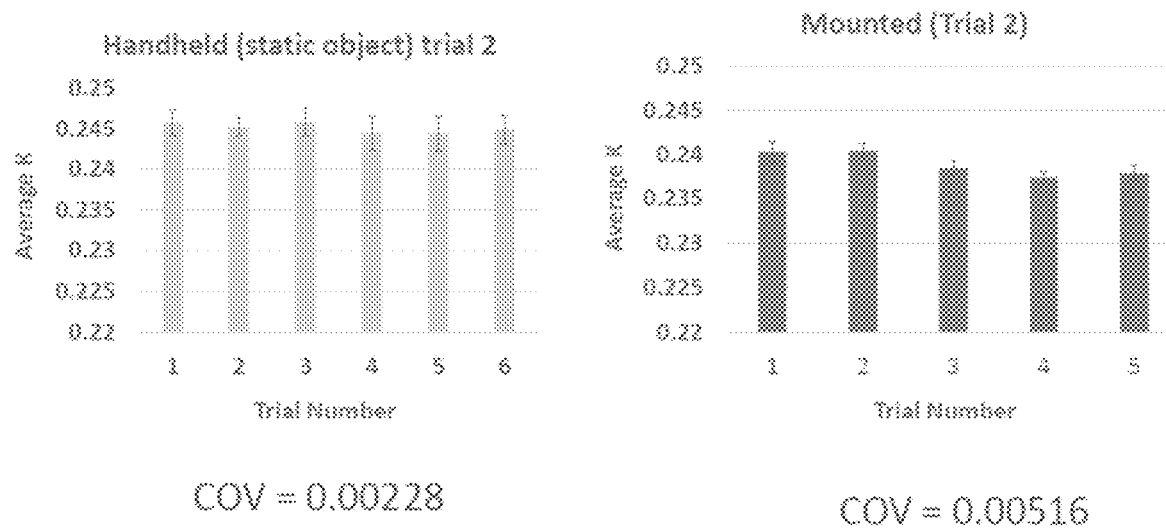
FIG. 19 depicts, in accordance with embodiments herein, charts describing repeatability measures.
Figure 20:
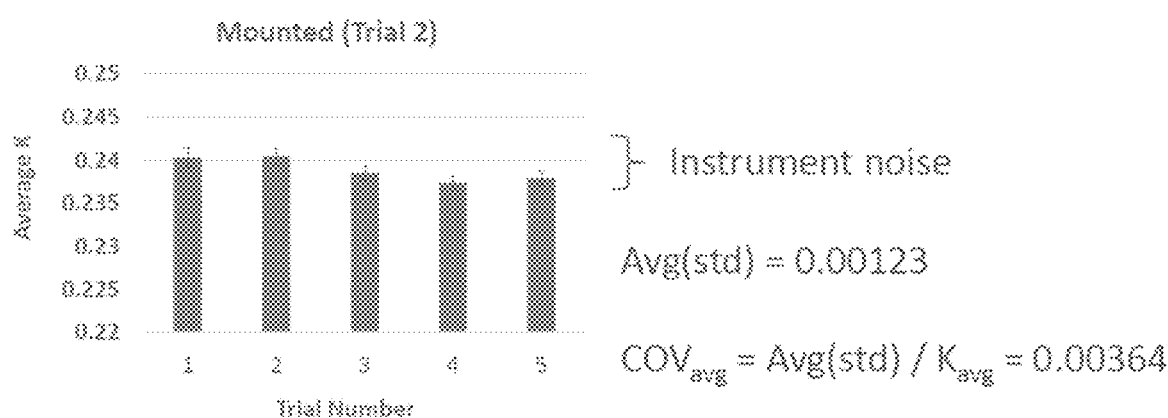
FIG. 20 depicts, in accordance with embodiments herein, charts describing instrument noise measurements.
Figure 21:
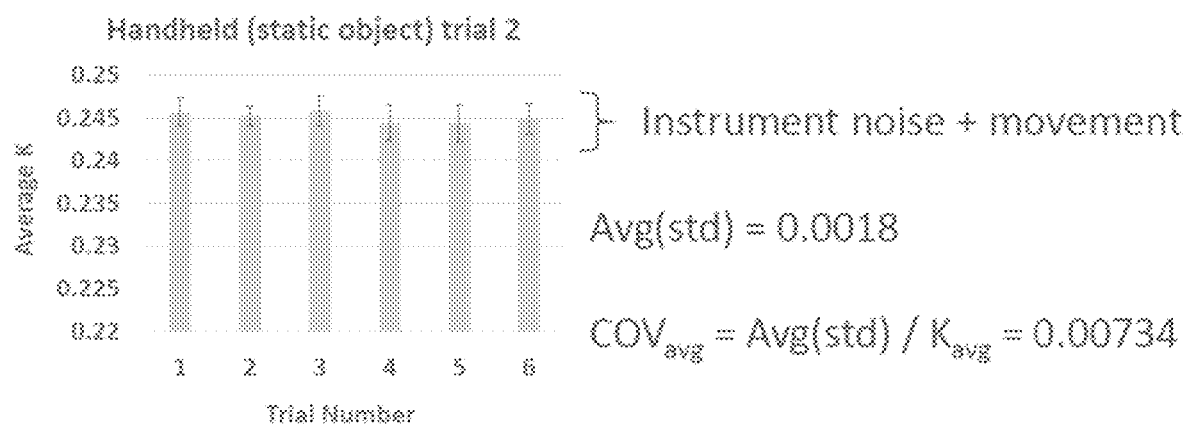
FIG. 21 depicts, in accordance with embodiments herein, movement noise.
Figure 22:
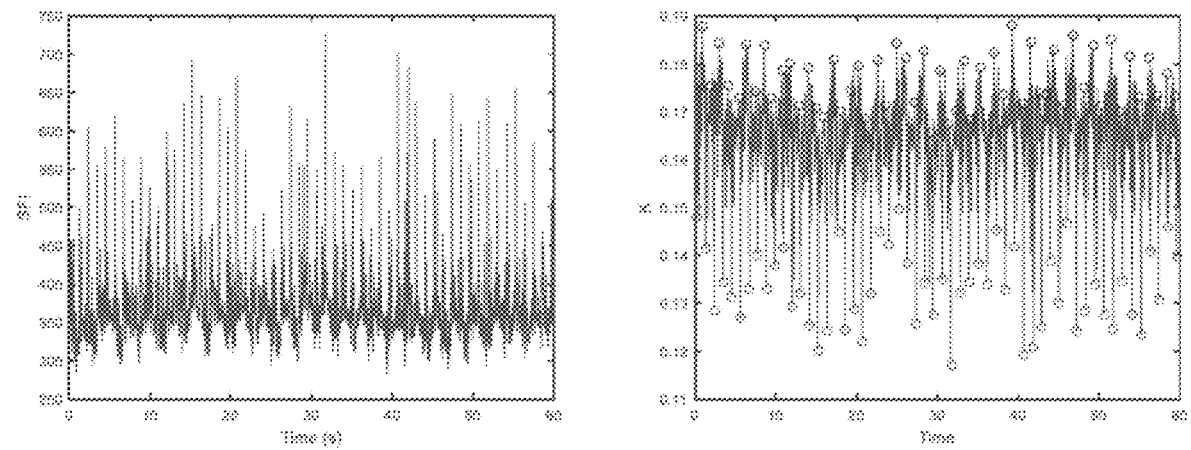
FIG. 22 depicts, in accordance with embodiments herein, signal measurements acquired from the skin showing periodic alternations in blood flow consistent with the heart beat. The amplitude of the plot at right was used for subsequent signal to noise computations.
Figure 27:
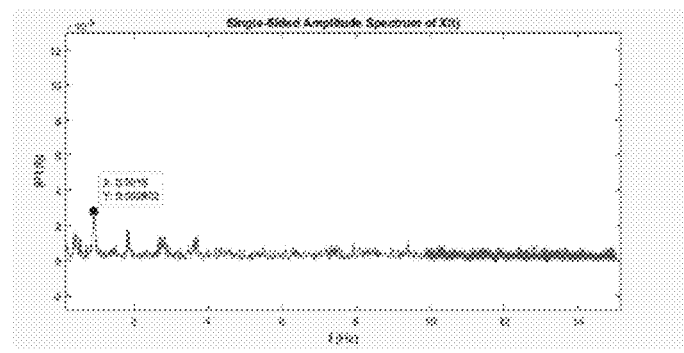
FIG. 27 depicts, in accordance with embodiments herein, signal to noise measurements from the forearm, fft version.
Figure 28:
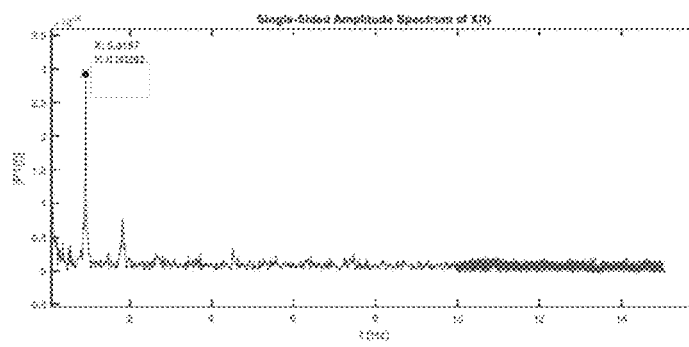
FIG. 28 depicts, in accordance with embodiments herein, signal to noise measurements from the finger, fft version.
Figure 29:
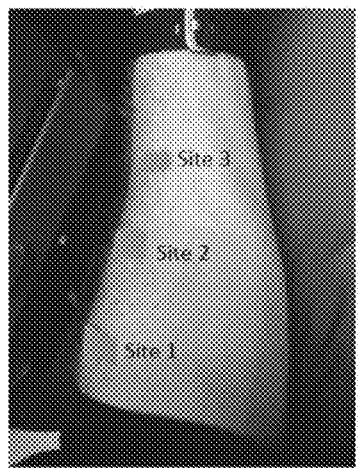
FIG. 29 depicts, in accordance with embodiments herein, charts describing measurements from three sites. Sites 1 and 3 were unperturbed. Site 2 was physically agitated to induce local hyperemia. Signal to noise ratio of 12.7:1.
Figure 29:
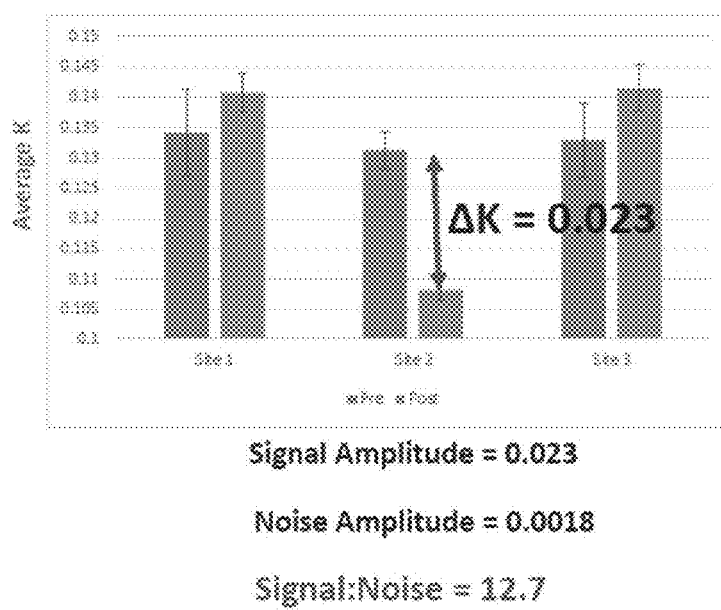

All references, publications, and patents cited herein are incorporated by reference in their entirety as though they are fully set forth. Unless defined otherwise, technical and scientific terms used herein have the same meaning as commonly understood by one of ordinary skill in the art to which this invention belongs. Hornyak, et al., Introduction to Nanoscience and Nanotechnology, CRC Press (2008); Singleton et al., Dictionary of Microbiology and Molecular Biology 3rd ed., J. Wiley & Sons (New York, N.Y. 2001); March, Advanced Organic Chemistry Reactions, Mechanisms and Structure 7th ed., J. Wiley & Sons (New York, N.Y. 2013); and Sambrook and Russel, Molecular Cloning: A Laboratory Manual 4th ed., Cold Spring Harbor Laboratory Press (Cold Spring Harbor, N.Y. 2012), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

As used herein, "LSI" refers to laser speckle imaging.

As described herein, the inventors have developed a compact, handheld dermatoscope that enables real time blood flow measurements of skin during conventional visual inspection. Its blood-flow measuring capabilities are equivalent to laboratory-grade devices, and its handheld nature enables it to be used in a routine manner. As further described herein, blood flow measurements were achieved by the inventors by integrating a compact laser speckle imaging (LSI) system into a dermatoscope. LSI measurements using illumination from a 785 nm laser diode was performed simultaneously with visual inspections under white LED illumination via spectral filtering of co-registered images. Flow measurements using the LSI-dermatoscope were validated by acquiring LSI data from a tissue-simulating phantom with syringe pump-controlled flow of optically scattering fluid across the physiologically relevant range. Measurements were also performed during post-occlusive reactive hyperemia tests (n=10) on the forearm of healthy volunteers to assess the correlation of the LSI-dermatoscope measurements to a validated benchtop LSI system and to perform repeatability and signal to noise analysis. The LSI-dermatoscope was able to measure known flow rates in a tissue-simulating phantom with a correlation coefficient of 0.98. Data acquired from volunteers during post-occlusive reactive hyperemia showed the expected physiological blood flow response of decreased blood flow during occlusion and the return of blood flow above baseline (hyperemia) following occlusion release. LSI-dermatoscope data was significantly correlated (p<0.05) to data acquired simultaneously using a traditional benchtop LSI system. The coefficient of variation between measurements was relatively low (0.0023) and exhibited a signal to noise ratio of 17:1.

In one embodiment, the present invention provides a device that combines blood flow measurements as well as visual inspection of a sample. In another embodiment, the device allows mapping of tissue. In another embodiment, the device is handheld. In another embodiment, the device allows simultaneous visual inspection and blood flow measurement and/or mapping of tissue. In another embodiment, the present invention provides a modified dermatoscope. In another embodiment, the device comprises a compact laser speckle imaging (LSI) system integrated into a dermatoscope.

In another embodiment, the present invention provides a method of providing functional information about tissue simultaneously with visual inspection. In another embodiment, the present invention provides a method of studying blood flow in pigmented lesions. In another embodiment, the present invention provides a method of imaging. In another embodiment, the present invention provides a method of treating a disease. In another embodiment, the present invention provides a method of screening for a disease. In another embodiment, the disease is cancer.

In another embodiment, the present invention provides a device, such as a lens, for visual inspection of a sample such as tissue, an apparatus for illumination such as for LSI illumination, a digital camera system and camera lens so that for example it may be used for LSI image acquisition, and an enclosure such as may be used to hold parts together in a compact device. In another embodiment, the device comprises a dermatoscope integrated with an LSI system.

In another embodiment, the device may be used for visually observing and quantifying blood flow changes in skin nevi. In another embodiment, the device may be used for cancer screening. In another embodiment, the device may be used for visually observing and quantifying blood flow changes associated with skin inflammation and/or irritation. In another embodiment, the device may be used for visually observing and quantifying blood flow changes associated with wounds or burns. In another embodiment, the device may be used for visually observing and quantifying blood flow changes associated with allergies. In another embodiment, the device may be used for visually observing and quantifying blood flow changes associated with scars. In another embodiment, the device may be used for visually observing and quantifying blood flow changes associated with infections. In another embodiment, the device may be used for visually observing and quantifying blood flow changes associated with dermatitis. In another embodiment, the device may be used for visually observing and quantifying blood flow changes associated with acne. In another embodiment, the device may be used for visually observing and quantifying blood flow changes associated with keratosis. In another embodiment, the device may be used for visually observing and quantifying blood flow changes associated with psoriasis. In another embodiment, the device may be used for visually observing and quantifying blood flow changes associated with Rosacea. In another embodiment, the method comprises simultaneous visual inspection and blood flow measurement. In another embodiment the method comprises simultaneous visual inspection and mapping of tissue blood flow and/or hemodynamics.

Various embodiments include a method of measuring blood flow in a subject, comprising obtaining laser speckle imaging (LSI) measurements, and validating flow measurements. In another embodiment, validating flow measurements comprises acquiring LSI data from a tissue-simulating phantom with syringe pump-controlled flow of optically scattering fluid across a physiologically relevant range. In another embodiment, the method provides a map of overall blood flow. In another embodiment, the method provides robust quantification of functional information of the subject. In another embodiment, the subject is a human.

EXAMPLES

Example 1

Generally

In accordance with various embodiments herein, the inventors have developed a compact, handheld dermatoscope that enables real time blood flow measurements of skin during conventional visual inspection. Its blood-flow measuring capabilities are equivalent to laboratory-grade devices, and its handheld nature enables it to be used in a routine manner.

As further described herein, blood flow measurements were achieved by the inventors by integrating a compact laser speckle imaging (LSI) system into a dermatoscope. LSI measurements using illumination from a 785 nm laser diode was performed simultaneously with visual inspections under white LED illumination via spectral filtering of co-registered images. Flow measurements using the LSI-dermatoscope were validated by acquiring LSI data from a tissue-simulating phantom with syringe pump-controlled flow of optically scattering fluid across the physiologically relevant range. Measurements were also performed during post-occlusive reactive hyperemia tests (n=10) on the forearm of healthy volunteers to assess the correlation of the LSI-dermatoscope measurements to a validated benchtop LSI system and to perform repeatability and signal to noise analysis.

The LSI-dermatoscope was able to measure known flow rates in a tissue-simulating phantom with a correlation coefficient of 0.98. Data acquired from volunteers during post-occlusive reactive hyperemia showed the expected physiological blood flow response of decreased blood flow during occlusion and the return of blood flow above baseline (hyperemia) following occlusion release. LSI-dermatoscope data was significantly correlated (p<0.05) to data acquired simultaneously using a traditional benchtop LSI system. The coefficient of variation between measurements was relatively low (0.0023) and exhibited a signal to noise ratio of 17:1.

Example 2

Advantages

In one embodiment, the present invention provides clinically-relevant functional information about tissue simultaneously with visual inspection, which is currently standard of care. Additionally, in another embodiment the present invention provides additional and valuable functionality to the dermatoscope. In another embodiment, the device is easier to operate, smaller, and considerably less expensive than current commercial technologies used to measure blood flow.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps, some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a," "an," and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

What is claimed is:

1. A device, comprising:
    a dermatoscope comprising an illuminating light source, and a magnifying optic, wherein the dermatoscope is integrated with a laser speckle imaging (LSI) system; and
    a beam splitter that is configured to direct light to the LSI system and to the magnifying optic of the dermatoscope,
    wherein the device allows real time blood flow measurements that improve diagnosis.

2. The device of claim 1, wherein the illuminating light source is a broadband light source.

3. The device of claim 1, wherein the device is handheld.

4. The device of claim 1, wherein the dermatoscope is configured to facilitate visual inspection by a user of a first area of a subject, and wherein the LSI system is configured to measure a second area of the subject that is co-localized with said first area.

5. The device of claim 1, wherein the device provides blood flow measurements of skin during visual inspection of a subject.

6. The device of claim 1, wherein the device provides functional information of tissue simultaneously with visual inspection of a subject.

7. The device of claim 6, wherein areas being visually inspected and measured using LSI are co-localized.

8. The device of claim 1, further comprising a CMOS camera.

* * * * *